US00PP33527P2

(12) United States Plant Patent
Van Swieten

(10) Patent No.: US PP33,527 P2
(45) Date of Patent: Sep. 28, 2021

(54) ***PHALAENOPSIS* ORCHID PLANT NAMED 'PHALIMUNG'**

(50) Latin Name: ***Phalaenopsis* hybrid**
Varietal Denomination: PHALIMUNG

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,218

(22) Filed: Apr. 15, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALIMUNG', particularly characterized by white, flecked flowers with greenish-yellow and white, dotted lips, flowers with a convex shape in lateral view, apical lobes of the lip with a small bump and ridge, and is propagated by meristem tissue culture, is disclosed.

3 Drawing Sheets

Genus and species: *Phalaenopsis* hybrid.
Variety denomination: 'PHALIMUNG'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALIMUNG'.

The new *Phalaenopsis* plant is a product of a planned breeding program conducted by the inventor in Bleiswijk, the Netherlands. The objective of this breeding program was to create a new *Phalaenopsis* plant with attractive, white, flecked flowers with greenish-yellow and white, dotted lips, suitable for potted plant production.

The new *Phalaenopsis* plant 'PHALIMUNG' is a result of cross-pollination made by the inventor in April 2012 in Bleiswijk, the Netherlands, of the proprietary female, or seed parent, *Phalaenopsis* hybrid 'PHALDANBO' (U.S. Plant Pat. No. 25,930) with the proprietary male, or pollen parent, *Phalaenopsis* hybrid '010070-02' (unpatented).

The new *Phalaenopsis* was selected by the inventor as a single plant within the progeny of the stated cross-pollination in a controlled greenhouse in Bleiswijk, the Netherlands, in March 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 30, 2020 (Application no. 2020/0296), by Applicant who obtained the subject matter disclosed directly from the inventor. 'PHALIMUNG' has not been made publicly available or sold anywhere in the world prior to the effective filing date of this application with the exception of sales or disclosures made one year or less before the effective filing date of this claimed invention by Applicant who obtained 'PHALIMUNG' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALIMUNG' as a new and distinct variety of *Phalaenopsis* plant:

1) White, flecked flowers with greenish-yellow and white, dotted lips (intensity and number of flecks depend on the temperature during growing period);
2) Flower shape in lateral view is convex; and
3) Apical lobe of the lip has a small bump and ridge.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2021. Colors in the photographs may differ from the color values cited in the detailed botanical description, which accurately describe the actual colors of the new variety.

DESCRIPTION OF THE NEW VARIETY

Figure 1:
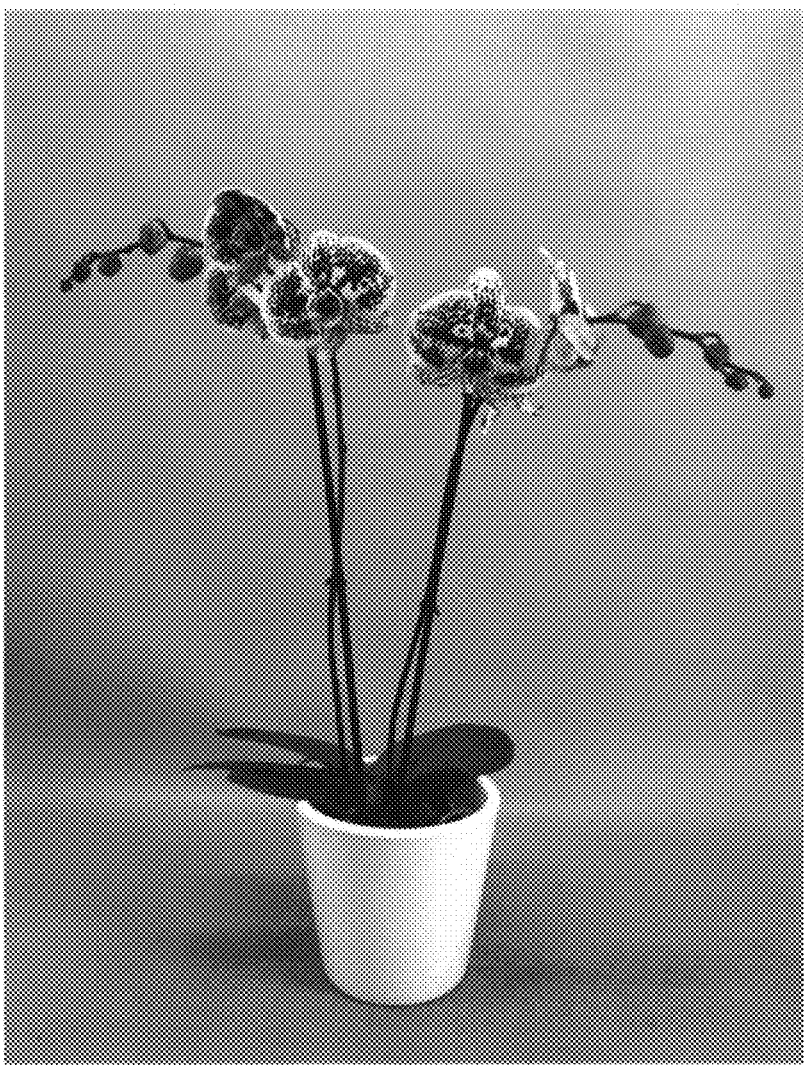
FIG. 1 shows the overall plant habit, including blooms, buds, and foliage of 'PHALIMUNG'.
Figure 2:
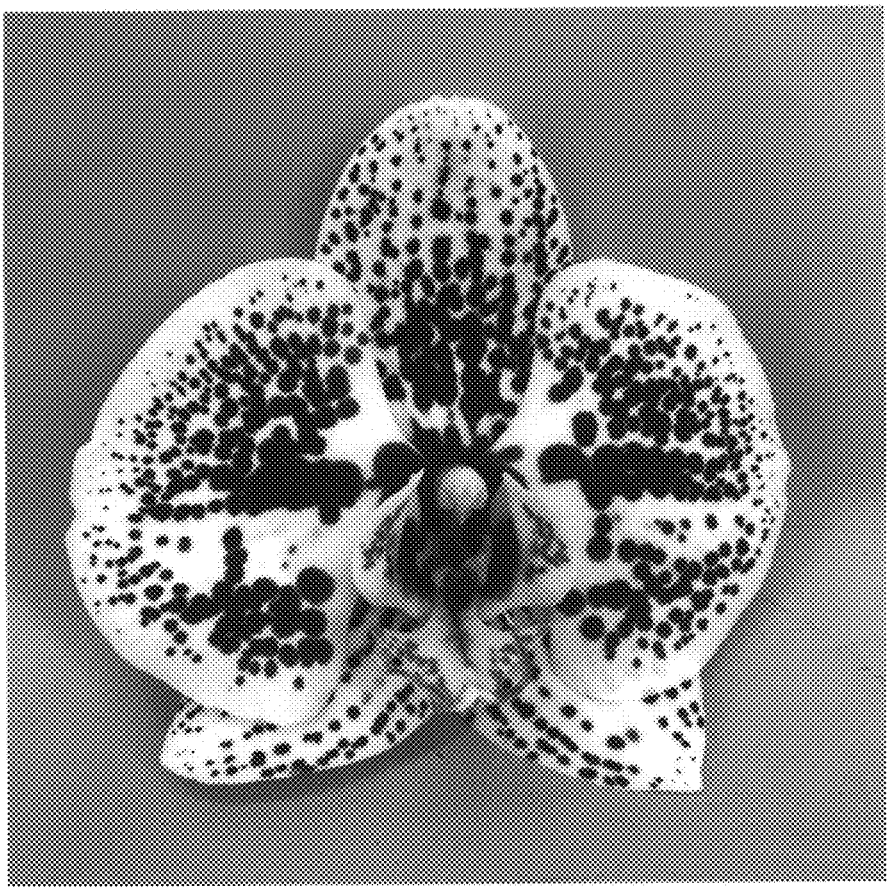
FIG. 2 shows a close-up of a flower of 'PHALIMUNG'.
Figure 3:
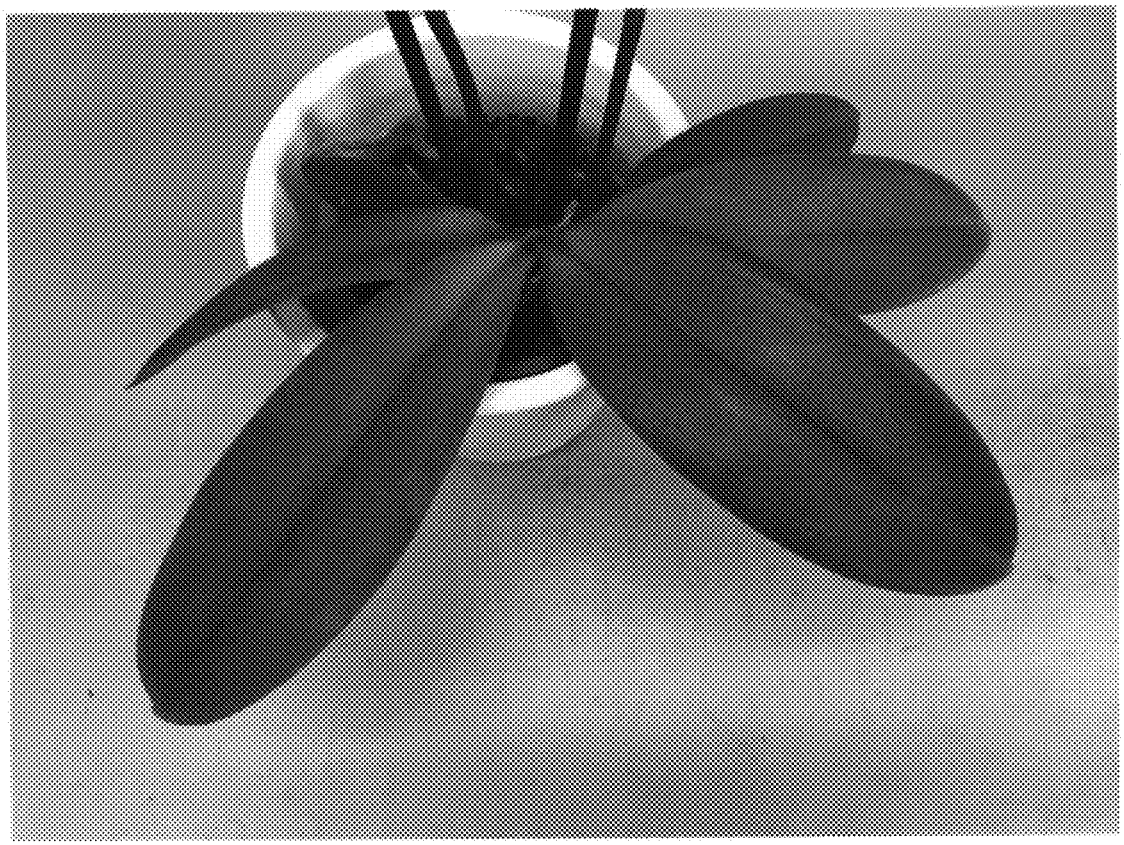
FIG. 3 shows an overhead view of the leaves of 'PHALIMUNG'.

The following detailed description sets forth the distinctive characteristics of 'PHALIMUNG'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALIMUNG'.

Parentage:

*Female parent*.—*Phalaenopsis* cultivar 'PHALDANBO' (U.S. Plant Pat. No. 25,930).

*Male parent*.—*Phalaenopsis* cultivar '010070-02' (unpatented).

Propagation:

*Type*.—Meristem tissue culture.

Roots:

*Root description*.—Greyed-green (a color in between RHS 190B and RHS 190C) colored roots with branching lateral roots having greenish-yellow (RHS N144D) with a touch of purplish-red (RHS N77B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height (from soil level to top of inflorescence)*.—Approximately 50.0 cm to 55.0 cm.

*Width (measured from leaf tips)*.—About 23.0 cm to 25.0 cm.

*Vigor*.—Strong.

Leaves:

*Mature leaves*.—Quantity per plant: 7 to 8 leaves are produced before flowering. Length (fully expanded): 16.0 cm to 18.0 cm. Width: 6.0 cm to 7.0 cm. Position of the broadest part of the leaf: At the middle. Shape: Oblong. Base shape: Moderately elongated. Apex: Obtuse asymmetric. Leaf blade angle with the petiole (measured from the horizontal position): Between 5 degrees and 15 degrees. Leaf margin: Entire. Color: Upper surface: Yellow-green (RHS 146A). Lower surface: Yellow-green (RHS 146B) with a touch of diluting dark purplish-red (RHS N79B). Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B with a touch of reddish-brown (RHS 177A).

Peduncle:

*Quantity per plant*.—1 to 2.

*Number of flowers per peduncle*.—8 to 10.

*Length*.—50.0 cm to 55.0 cm.

*Diameter*.—4.0 mm to 5.0 mm.

*Strength*.—Strong.

*Aspect*.—Upright to slightly pendent.

*Texture*.—Smooth.

*Color*.—Greyish-purple (RHS N77A) with a hint of yellow-green (RHS 146D).

*Internode length*.—4.0 cm to 5.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 180.0 mm to 230.0 mm.

*Flowering time*.—First flowers can be expected 10 to 11 months after planting in a 12-cm pot.

*Flower*.—Height: 85.0 mm to 90.0 mm. Diameter: 88.0 mm to 93.0 mm. Depth of lip: 20.0 mm to 22.0 mm.

*Flower longevity*.—On the plant: 11 to 14 weeks.

*Flower shape*.—Convex.

*Fragrance*.—Absent.

*Flower bud*.—Average size: Medium to large. Length: 21.0 mm to 23.0 mm. Width: 19.0 mm to 21.0 mm. Shape: Egg shaped. Color: Yellow-green (a mix of RHS N144D and RHS 145C) with a purplish-red shade (RHS N77B) and greyish-purple flecks (RHS N77A).

*Petals*.—Arrangement: Open/free. Shape: Semi-circular. Apex: Emarginated asymmetric. Margin: Moderately undulated. Length (from base to tip): 42.0 mm to 44.0 mm. Width: 55.0 mm to 57.0 mm. Position of the broadest part of the petal: Toward the base. Color (when fully opened): Upper surface: Basic color: White (RHS NN155C). Over color: Dark red-purple flecks (a mix of RHS 187B and RHS N79C). Lower surface: Basic color: White (RHS NN155C). Over color: Light purple (RHS 76A); diluting flecks (a mix of RHS N79B and RHS N77B). Number of spots, flecks, and stripes on the petals (upper surface): Many flecks. Color of spots, flecks, and stripes on the petals (upper surface): A mix of RHS 187B and RHS N79C. Density of netting of the petals (upper surface): None. Color of the netting (upper surface): Not applicable.

*Dorsal sepal*.—Shape: Broad elliptic. Apex: Emarginated symmetric. Margin: Entire. Length (from base to tip): 48.0 mm to 50.0 mm. Width: 32.0 mm to 34.0 mm. Position of the broadest part of the dorsal sepals: At the middle. Color (when fully opened): Upper surface: Basic color: White (RHS NN155C). Over color: Dark red flecks (a mix of RHS 187A and RHS 187B). Lower surface: Basic color: White (RHS NN155C). Over color: Light yellow-green (RHS 145D) and touch of light reddish-purple (RHS N78D); diluting dark purple flecks (RHS N79B).

Number of spots, flecks, and stripes on the dorsal sepals (upper surface): Many to very many flecks. Color of spots, flecks, and stripes on the dorsal sepals (upper surface): A mix of RHS 187A and RHS 187B. Density of netting of the dorsal sepals (upper surface): None. Color of the netting: Not applicable.

*Lateral sepals*.—Shape: Ovate. Apex: Obtuse asymmetric. Margin: Entire. Length (from base to tip): 46.0 mm to 48.0 mm. Width: 33.0 mm to 35.0 mm. Position of the broadest part of the lateral sepals: Toward the base. Color (when fully opened): Upper surface: Basic color: White (RHS NN155C). Over color: Touch of light yellow-green (RHS 145D) at the base; dark red flecks (a mix of RHS 187A and RHS 187B). Lower surface: Basic color: White (RHS NN155C). Over color: Light yellow-green (RHS 145D); very light purple (RHS 76B) toward the tip; light reddish-purple midvein (RHS N78D); diluting stripes (RHS N79B). Number of spots, flecks, and stripes on the lateral sepals (upper surface): Many flecks. Color of spots, flecks, and stripes on the lateral sepals (upper surface): A mix of RHS 187A and RHS 187B. Density of netting of the lateral sepals (upper surface): None. Color of the netting (upper surface): Not applicable.

*Labellum* (*lip*).—Whiskers: Present. Length of whiskers: 10.0 mm to 12.0 mm. Color of whiskers: Very light purple (RHS 76B); flecked (RHS N79C) with white tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 19.0 mm to 21.0 mm. Width: 9.0 mm to 11.0 mm. Color: Upper surface: Dark red fleck (RHS 187A) at the base; greenish-yellow (RHS 6B) on one side toward margin; white (RHS NN155C); striped (RHS N78A) toward the other margin and tip. Lower surface: Very light purple (RHS 76C) at the base; greenish-yellow (RHS 6C) on one side toward margin and white (RHS NN155C) toward the other margin and tip; diluting purplish-red stripes (RHS N77B). Number of spots, flecks, and stripes on the lateral lobe: One fleck at the base; medium stripes. Color of spots, flecks, and stripes on the lateral lobe: Fleck (RHS 187A); stripes (RHS N78A). Density of netting of the lateral lobe: None. Color of the netting: Not applicable.

*Apical lobe*.—Shape: Trullate. Margin: Entire. Length: 17.0 mm to 19.0 mm. Width: 19.0 mm to 21.0 mm. Color: Upper surface: Dark red margin (RHS 187B) and greenish-yellow (RHS 4A) at the base; white (RHS NN155C) toward whiskers; dots (a color in between RHS N77B and RHS N79C) and dark red midvein (RHS 187B). Lower surface: Dark red margin (RHS 187B) at the base and greenish-yellow wings (RHS 4A); white (RHS NN155C) at the middle from base toward whiskers; diluting dots (RHS N77B) toward margins. Number of spots, dots, and stripes on the apical lobe: Medium dots. Color of spots, dots, and stripes on the apical lobe: A color in between RHS N77B and RHS N79C. Density of netting of the apical lobe: None. Color of the netting: Not applicable. Bump and ridge: Present (small).

*Callus*.—Average size: Medium to large. Height: 7.0 mm to 8.0 mm. Length: 6.0 mm to 7.0 mm. Width: 3.0 mm to 4.0 mm. Color: Dark red (RHS 187A) at the middle with yellow tips (RHS 13A) and yellowish-grey (RHS 156C) on sides.

Reproductive organs:

*Column*.—Length: 8.0 mm to 10.0 mm. Diameter: 5.0 mm to 6.0 mm. Color: Purplish-pink (RHS N78C); flecked (RHS N79C) with white tip (RHS NN155C).

*Pollinia*.—Quantity: 2. Diameter: 1.1 mm to 1.3 mm. Color: Orange (RHS 25A).

*Ovary*.—Length: 10.0 mm to 12.0 mm. Diameter: 2.5 mm to 2.9 mm.

*Pedicel*.—Length: 40.0 mm to 42.0 mm. Diameter: 3.0 mm to 3.3 mm. Color: Dark purplish-red (RHS N79B) at the base; light yellow-green (RHS 145C) and touch of light reddish-purple (RHS N78D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALIMUNG' differs from the female parent plant 'PHALDANBO' (U.S. Plant Pat. No. 25,930) in that 'PHALIMUNG' has flowers with a flecked pattern and medium curvature of the lateral lobe, whereas 'PHALDANBO' has flowers with an even pattern and weak curvature of the lateral lobe. Additionally, 'PHALIMUNG' has larger flowers than 'PHALDANBO'.

'PHALIMUNG' differs from the male parent plant '010070-02' (unpatented) in that 'PHALIMUNG' has flowers with a flecked pattern and columns that are purplish-pink and flecked with white tips, whereas '010070-02' has flowers with a flecked and edged pattern and columns that are white with a reddish-purple region at the middle.

'PHALIMUNG' is most similar to the commercial *Phalaenopsis* plants named 'PHALGRYCHI' (U.S. Plant Pat. No. 31,806) and 'PHALGYTCAN' (U.S. Plant Pat. No. 32,282). 'PHALIMUNG' differs from the commercial variety 'PHALGRYCHI' in that 'PHALIMUNG' has columns that are purplish-pink and flecked with white tips and whiskers that are very light purple and flecked with white tips, whereas 'PHALGRYCHI' has white columns and whiskers that are white and flecked with light greenish-yellow tips. Additionally, 'PHALIMUNG' has smaller flowers and narrower leaves than 'PHALGRYCHI'.

'PHALIMUNG' differs from the commercial variety 'PHALGYTCAN' in that 'PHALIMUNG' has columns that are purplish-pink and flecked with white tips and whiskers that are very light purple and flecked with white tips, whereas 'PHALGYTCAN' has columns that are very light purple and purple toward margins with white tips and light yellow whiskers. Additionally, 'PHALIMUNG' has wider leaves than 'PHALGYTCAN'.

I claim:

1. A new and distinct variety of *Phalaenopsis* plant named 'PHALIMUNG', substantially as described and illustrated herein.

* * * * *